US00PP32600P2

(12) United States Plant Patent
Bak et al.

(10) Patent No.: US PP32,600 P2
(45) Date of Patent: Dec. 8, 2020

(54) ***GUZMANIA* 'CROWN'**

(50) Latin Name: *Guzmania*
Varietal Denomination: CROWN

(71) Applicant: Corn Bak B.V., Assendelft (NL)

(72) Inventors: Elly Bak, Rijsenhout (NL); Nicolaas D. M. Steur, Oude Niedorp (NL)

(73) Assignee: Corn Bak. B.V.

( * ) Notice: Subject to any disclaimer, the term of this patent is extended or adjusted under 35 U.S.C. 154(b) by 0 days.

(21) Appl. No.: 16/873,175

(22) Filed: Feb. 18, 2020

(51) Int. Cl.
*A01H 6/22* (2018.01)
*A01H 5/00* (2018.01)

(52) U.S. Cl.
USPC ..... Plt./371

(58) Field of Classification Search
USPC ..... Plt./371
CPC ..... A01H 6/22; A01H 5/00
See application file for complete search history.

(56) References Cited

PUBLICATIONS

PLTO Plant Variety Database Aug. 8, 2020.*

* cited by examiner

*Primary Examiner* — Annette H Para
(74) *Attorney, Agent, or Firm* — Cassandra Bright

(57) ABSTRACT

A new and distinct cultivar of *Guzmania* plant named 'CROWN' characterized by a solid growth habit; funnel-form rosette plant, measuring about 42 cm in height (above the pot when flowering), numerous green color foliage (measuring about 50 to 60 cm in length and about 9 cm in width), and superior floral bract production. Bracts have a unique red inflorescence (RHS 44A), branched head inflorescence (measuring about 10 cm in height and about 10 cm in diameter), and long-lasting habit. The new variety is a *Guzmania*, typically produced as an indoor ornamental plant.

2 Drawing Sheets

Latin name of the genus: *Guzmania*.
Variety denomination: 'CROWN'.

BACKGROUND OF THE INVENTION

The present invention relates to a new and distinct hybrid cultivar of *Guzmania* plant, botanically known as *Guzmania* sp., of the family Bromeliaceae, and hereinafter referred to as 'CROWN'. *Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'CROWN' originated from a cross made in a controlled breeding program by the inventors in 2003. The female or seed parent is the unnamed *Guzmania* selection identified by code 03048301 (unpatented). The male or pollen parent is the unnamed *Guzmania* selection identified by code 03048347 (unpatented). The new *Guzmania* 'CROWN' was discovered and selected by the inventors in 2007 as a single flowering plant within the progeny of the stated cross in a controlled environment in Assendelft, The Netherlands.

Asexual reproduction of the new *Guzmania* cultivar was first performed by off-shoots beginning in 2008 and then by tissue culture beginning in 2015 in Assendelft, The Netherlands, with first flowering after asexual reproduction occurring in 2019 in Assendelft, The Netherlands. Asexual reproduction of the *Guzmania* 'CROWN' has demonstrated that the combination of characteristics as herein disclosed for the new cultivar are firmly fixed and retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey', Berlin (1986); and Rauh, Werner, BROMELIEN, Verlag Eugen Ulmer, Stuttgart (1981).

SUMMARY OF THE INVENTION

The following traits have been repeatedly observed and are determined to be unique characteristics of 'CROWN' which in combination distinguish this *Guzmania* as a new and distinct cultivar:

1. Solid growth habit.
2. Funnel-form rosette plant, measuring about 42 cm in height (above the pot when flowering).

3. Numerous, green colored foliage, measuring about 50-60 cm in length and about 6-9 cm in width.
4. Superior floral bract production.
5. Unique red inflorescence (RHS 44A).
6. Branched head inflorescence, measuring from about 10 cm in height and about 10 cm in diameter.
7. Long-lasting habit.

PARENTAL COMPARISON

Plants of the parental *Guzmania* selection identified by code 03048301 and *Guzmania* selection identified by code 03048347 (both unpatented) are no longer available to provide a botanical comparison with the new *Guzmania* hybrid 'CROWN'.

COMMERCIAL COMPARISON

There are no known comparison cultivars.

BRIEF DESCRIPTION OF THE PHOTOGRAPHS

The accompanying photographs illustrate the overall appearance of the new *Guzmania* hybrid 'CROWN' showing the colors as true as is reasonably possible with colored reproductions of this type. Colors in the photograph may differ slightly from the color values cited in the detailed botanical description which accurately describes the color of 'CROWN'.

DETAILED BOTANICAL DESCRIPTION

Figure 1:
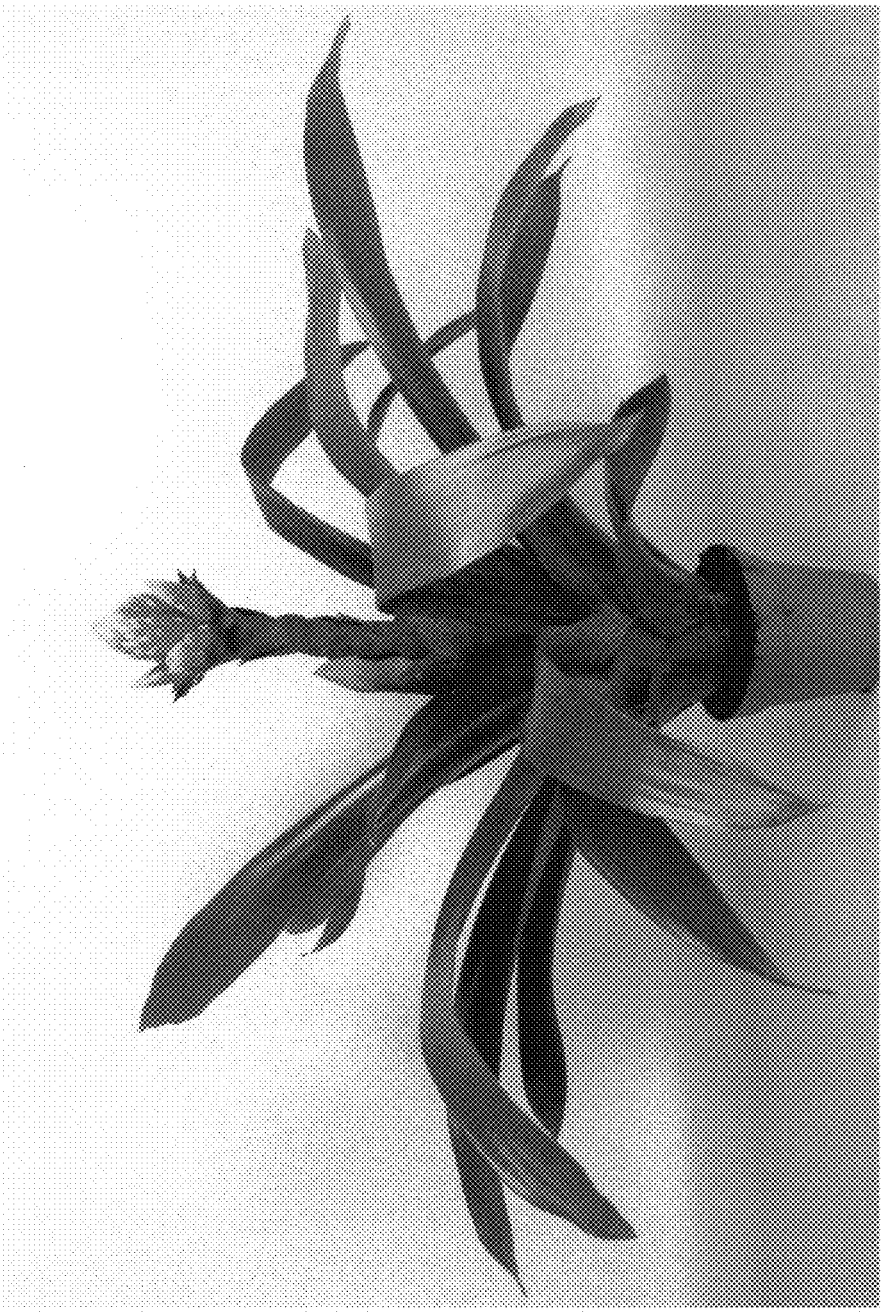
FIG. 1 shows a side view perspective of the primary and top bracts produced by a typical potted, flowering plant of 'CROWN', at 15 months of age from potting size.
Figure 2:
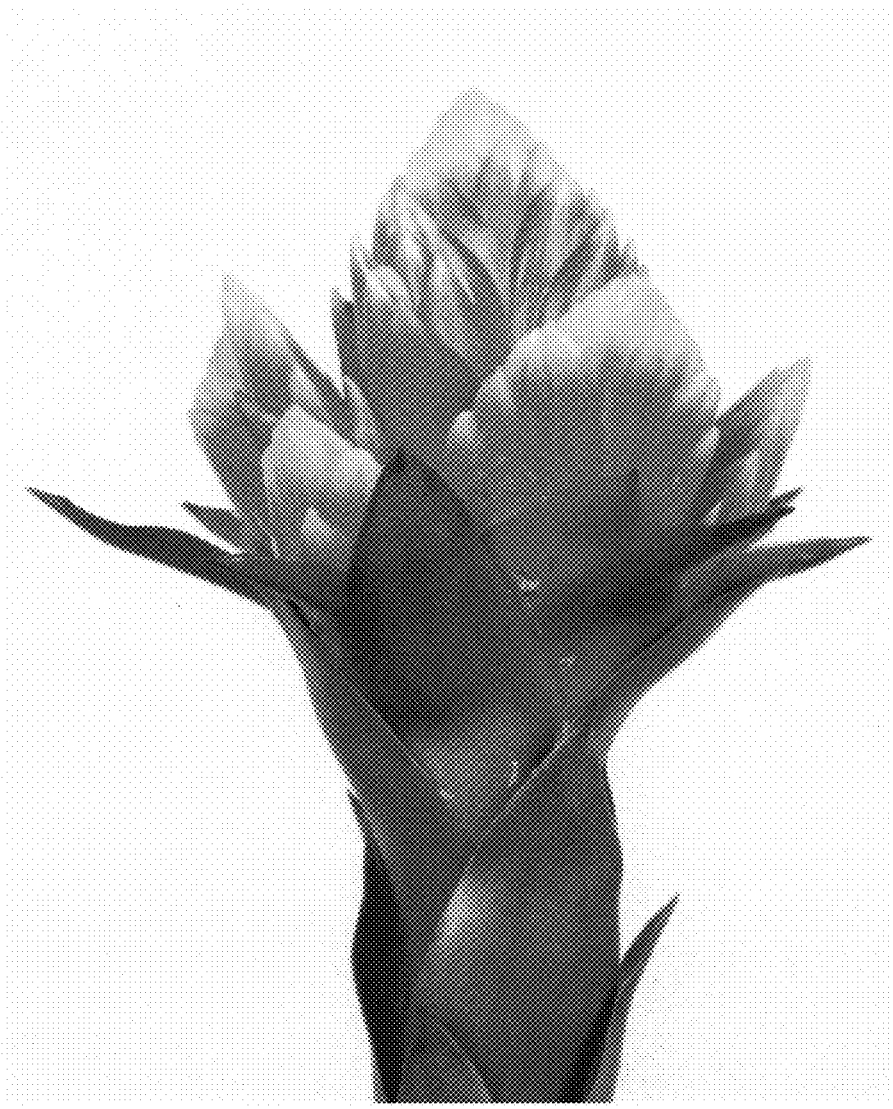
FIG. 2 shows a close-up side view perspective of the inflorescence and top bracts produced by a typical potted, flowering plant of 'CROWN', at 15 months of age from potting size.

'CROWN' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant. The aforementioned photographs, together with the following observations, measurements and values describe the new *Guzmania* 'CROWN' as grown in a greenhouse in Assendelft, The Netherlands, under conditions which closely approximate those generally used in commercial practice. Plants of 'CROWN' were grown in a greenhouse with day temperatures ranging from 20° C. to 28° C. and night temperatures ranging from 18° C. to 23° C. No artificial lighting or photoperiodic treatments were conducted, but plants of 'CROWN' are forced into flowering. The following fertilizer is added when growing plants of 'CROWN': 1 part nitrogen, 0.6 parts phosphor, 2 parts Kalium and 0.1 parts magnesium. Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'CROWN' described is about 17 weeks after flowering treatment.

Botanical classification: *Guzmania* sp.

Plant:

*Height*.—About 42 cm (when flowering).
*Width*.—About 75 cm.
*Shape*.—Funnel form rosette.
*Growth habit*.—Stemless.
*Plant vigor*.—Good.
*Flowering season*.—A fully grown plant can flower year-round, starting 18 weeks after induction of natural light or through flowering treatment.
*Cold tolerance*.—Frost tender. Temperatures below 5° C. may damage plants.
*Fragrance*.—None.

Foliage:

*Quantity*.—About 18 (depending on the size of the plant).
*Size of leaf*.—Length: About 50 to 60 cm (when flowering). Width: About 9 cm.
*Overall shape*.—Linear-lanceolate.
*Apex shape*.—Acute.
*Base shape*.—Strap-like around central axis.
*Margin*.—Entire.
*Texture* (*both surfaces*).—Smooth.
*Orientation*.—Leaf blades arch continuously from base.
*Color*.—Leaf color can vary somewhat depending on growing conditions. Mature: Upper surface: RHS Green 137A. Under surface: RHS Green 137C with anthocyanin.
*Venation*.—None.

Inflorescence:

*Borne*.—Erect stalks.
*Shape*.—Branched head.
*Size*.—Length: About 45 cm. Diameter: About 10 cm.
*Time of bloom*.—A fully grown plant can produce an inflorescence containing about 160 flowers (depending on the size of the plants), and can bloom the whole year starting about 18 weeks after natural induction or through flowering treatment.
*Duration of bloom*.—Each flower blooms one (1) day and the total blooming of the whole inflorescence is about 20 weeks.

Flowers: Not visible during anthesis.

Petals:

*Number*.—3 per flower.
*Length*.—About 4.8 cm.
*Width*.—About 0.6 cm.
*Overall shape*.—Ligulate.
*Apex shape*.—Obtuse.
*Base shape*.—Fused.
*Color*.—Upper and Under surfaces: RHS Yellow 7A.

Sepals:

*Number*.—3 per flower.
*Length*.—About 3 cm.
*Width*.—About 0.5 cm.
*Overall shape*.—Ligulate.
*Apex shape*.—Acute.
*Base shape*.—Fused.
*Color*.—RHS Yellow 7A.

Bracts:

Scape bracts:

*Quantity*.—About 13.

*Arrangement*.—Alternate.

*Size*.—Length: About 20 cm (lowest) to about 7.5 cm (scape bracts positioned just below the primary bracts). Width: About 5.2 cm.

*Overall shape*.—Lanceolate.

*Apex shape*.—Acute.

*Base shape*.—Fused.

*Margin*.—Entire.

*Texture*.—Smooth.

*Color*.—Upper surface: RHS Green 137C with Red 46A, apex Greyed-Purple 187A. Under surface: RHS Green 137C with Red 46A, apex Greyed-Purple 187A.

Primary bracts:

*Quantity*.—About 8.

*Arrangement*.—Alternate.

*Size*.—Length: About 5.5 cm. Width: About 3.5 cm.

*Overall shape*.—Lanceolate.

*Apex shape*.—Acute.

*Base shape*.—Fused.

*Margin*.—Entire.

*Texture*.—Smooth.

*Color*.—Upper and Under surfaces: RHS Red 46A, apex Greyed-Purple 187A.

Floral bracts:

*Quantity*.—About 160.

*Size*.—Length: About 5 cm. Width: About 2 cm.

*Overall shape*.—Lanceolate.

*Apex shape*.—Obtuse.

*Base shape*.—Fused.

*Margin*.—Entire.

*Texture*.—Smooth.

*Color*.—Lower floral bracts: Upper and Under surfaces: RHS Red 44A. Higher floral bracts: Upper and Under surfaces: RHS Red 44A with Yellow 8C to 7A.

Reproductive organs:

Androecium:

*Stamen*.—Number: 6 per flower. Length: About 4.5 cm. Diameter: About 0.1 mm. Color: RHS Yellow 7A.

*Anther*.—Length: About 0.5 cm. Color: RHS Greyed-Yellow 161C.

*Pollen*.—None.

Gynoecium:

*Pistil*.—Number: 1 per flower. Length: About 3 cm.

*Stigma*.—Shape: 3-parted. Width: About 2 mm. Color: Green, (too small to qualify R.H.S. value).

*Style*.—Length: About 3 cm. Color: Yellow (too small to qualify R.H.S. value).

*Ovary*.—Position: Superior. Shape: Conical. Length: About 0.9 cm. Diameter: About 0.4 cm. Color: White (too small to qualify R.H.S. value).

Other characteristics:

Seeds/fruit: Sterile hybrid, therefore, no seed or fruit produced.

Disease/pest resistance: No observations made.

Disease/pest susceptibility: No observations made.

What is claimed is:

1. A new and distinct cultivar of *Guzmania* plant named 'CROWN' as herein illustrated and described.

* * * * *